US00PP13967P39

(12) United States Plant Patent
Lopez

(10) Patent No.: US PP13,967 P3
(45) Date of Patent: Jul. 15, 2003

(54) STRAWBERRY PLANT NAMED 'PLARIONFRE'

(75) Inventor: Jose Miguel Arias Lopez, Navarra (ES)

(73) Assignee: Plantas de Navarra S.A. (ES)

( * ) Notice: Subject to any disclaimer, the term of this patent is extended or adjusted under 35 U.S.C. 154(b) by 73 days.

(21) Appl. No.: 09/796,024

(22) Filed: Feb. 28, 2001

(65) Prior Publication Data

US 2002/0059665 P1 May 16, 2002

(30) Foreign Application Priority Data

Jul. 28, 2000 (EP) ..... 2000/1176

(51) Int. Cl.[7] ..... A01H 5/00

(52) U.S. Cl. ..... Plt./208

(58) Field of Search ..... Plt./208, 209

(56) References Cited

PUBLICATIONS

Plantas De Navarra S.A., 'PLARIONFRE' Commercial Strawberry Varieties List; May 23, 2000; application no. 2000 / 1176; Spain.

2000/1176. Jul. 28, 2000, Register of Community Plant Variety Rights (European Community Plant Variety Office).

*Primary Examiner*—Bruce R. Campell
*Assistant Examiner*—June Hwu
(74) *Attorney, Agent, or Firm*—Christie, Parker & Hale, LLP

(57) ABSTRACT

'PLARIONFRE' is a new variety of strawberry having inflorecence above the foliage and conical-shaped fruit.

11 Drawing Sheets

BACKGROUND OF THE INVENTION

The new variety of strawberry was created in a breeding program by crossing two parents; in particular, by crossing as seed parent an undistributed, unpatented variety internally designated 9244 and as pollen parent an undistributed and unpatented variety internally designated 86-032. Both parental varieties are proprietary and have not been commercialized or distributed. The new variety and their parents are in the genus *Fragaria L.*

The resulting seedling of the new variety was grown and asexually propagated by runners in Soria, Spain, 3° W., 41° N., 3,000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The new variety differs from its seed parent in producing more firm fruit and earlier; and differs from the pollen parent in producing earlier fruit.

SUMMARY OF THE INVENTION

The present invention relates to a new and distinct strawberry variety. Having the varietal denomination of the new variety 'PLARIONFRE'. Among the characteristics which distinguish the new variety from other varieties of which I am aware are a combination of traits that include inflorescence which appears above the foliage and abundant production of red colored, conical shaped fruit.

COMPARISON TO CLOSEST VARIETY

The new variety is closest to the variety 'Camarosa' (U.S. Plant Pat. No. 8,708), but is distinguished therefrom by the following characteristics possessed by 'PLARIONFRE' which are different than, or not possessed by, 'Camarosa'.

1. 'Camarosa' exhibits more plant vigor than 'PLARIONFRE'.

2. 'Camarosa' exhibits more globose plant habit than 'PLARIONFRE'.

3. Leaf surface undulation of 'Camarosa' is weaker than 'PLARIONFRE'.

4. 'Camarosa' has a darker green upperside leaf color (near 141 B to 141 A) than 'PLARIONFRE' (near 143 B to 143 A) . The differences in the leaves of 'Camarosa' and the new variety are shown in FIGS. 1, 2, 3, and 4. These differences are maintained during the growing season.

5. In 'PLARIONFRE' the position of the inflorescence is above the foliage whereas in 'Camarosa', the inflorescence is level with the foliage.

6. Fruit of 'Camarosa' are larger than 'PLARIONFRE'.

7. Fruit of 'Camarosa' is almost cylindrical in shape, whereas fruit of 'PLARIONFRE' is conical.

8. Fruit of 'Camarosa' is dark red near 47B to 47A, whereas fruit of 'PLARIONFRE' is near 43A to 42A.

9. The differences in the fruit of 'Camarosa' and of the new variety are shown in FIGS. 8, 9, 10, and 11. These differences are maintained during the harvest season.

10. Time of flowering for 'PLARIONFRE' is earlier than from 'Camarosa' in the same location.

11. Time of fruit ripening for 'PLARIONFRE' is earlier than for 'Camarosa' in the same location.

12. 'PLARIONFRE' fruit is less firm than 'Camarosa' fruit.

BRIEF DESCRIPTION OF ILLUSTRATIONS

The accompanying photographs show typical specimens of the new variety, designated 96.09.812 in the illustrations, including fruit, foliage and flower, in color as nearly true as it is reasonably possible to make in color illustrations of this character. The reference to 'Camarosa' is as a "prior art".

DESCRIPTION OF THE NEW VARIETY

The following detailed description of the new variety is based upon observations taken of plants and fruits grown 'underglass', i.e. under tunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.). The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other know methods of propagating strawberry plants may be used. Strawberries root well after transplanting.

The term 'blistering' used herein refers to the texture or rugosity or surface ondulation inherent to leaves and is generally a constant characteristic.

GENERAL

'PLARIONFRE' is a short day variety that needs an induction to flowering by chilling, such as occurs at a high elevation nursery (fresh plant) or with cold storage (referred to as a frigo). Usually a short time is sufficient. 'PLARIONFRE' is self-fertile. It produces large quantity of pollen throughout the seasons and pollination is generally good as there are very few malformed fruit.

Production: Plants described are from high elevation nursery in Soria, Spain (3° W., 41° N, 3,000 feet elevation) Fruit trials are from nursery in Cartaya (Huelva), Spain (7° W., 37° N, 45 feet elevation).
Date of planting: Oct. 22, 1999.
Number of repetitions: 2.
Plants per repetition: 375.

Figure 1:
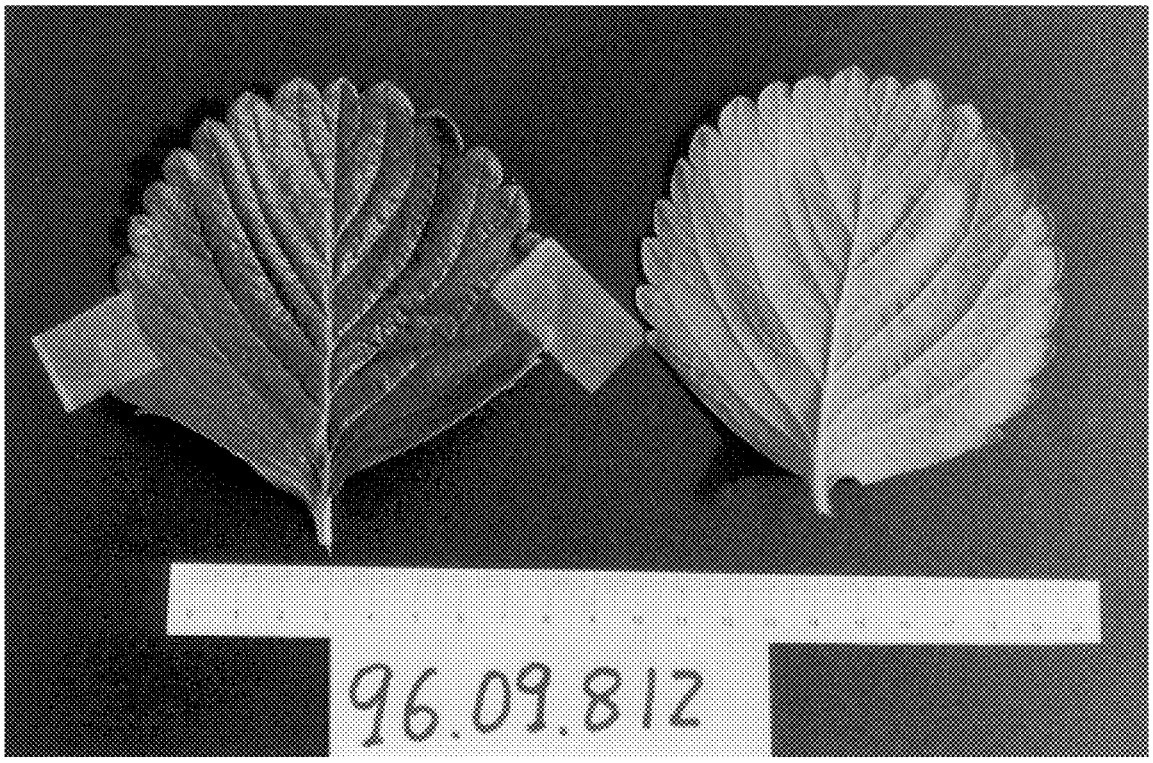
FIG. 1 shows the top and undersurface of a typical foliole of the new variety (designated 96.09.812) with the surface undulation of the upperside weaker and less dark green than the upperside of 'Camarosa'.
Figure 2:
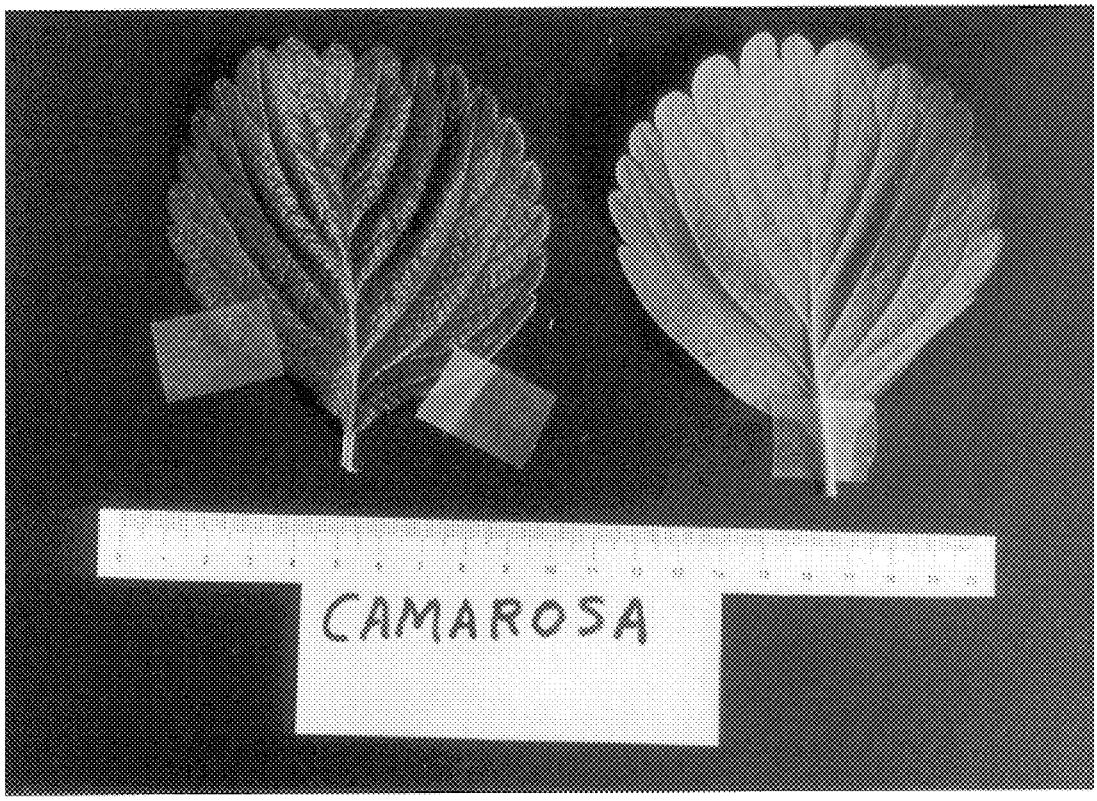
FIG. 2 shows the top and undersurface of a typical foliole of 'Camarosa'.
Figure 3:
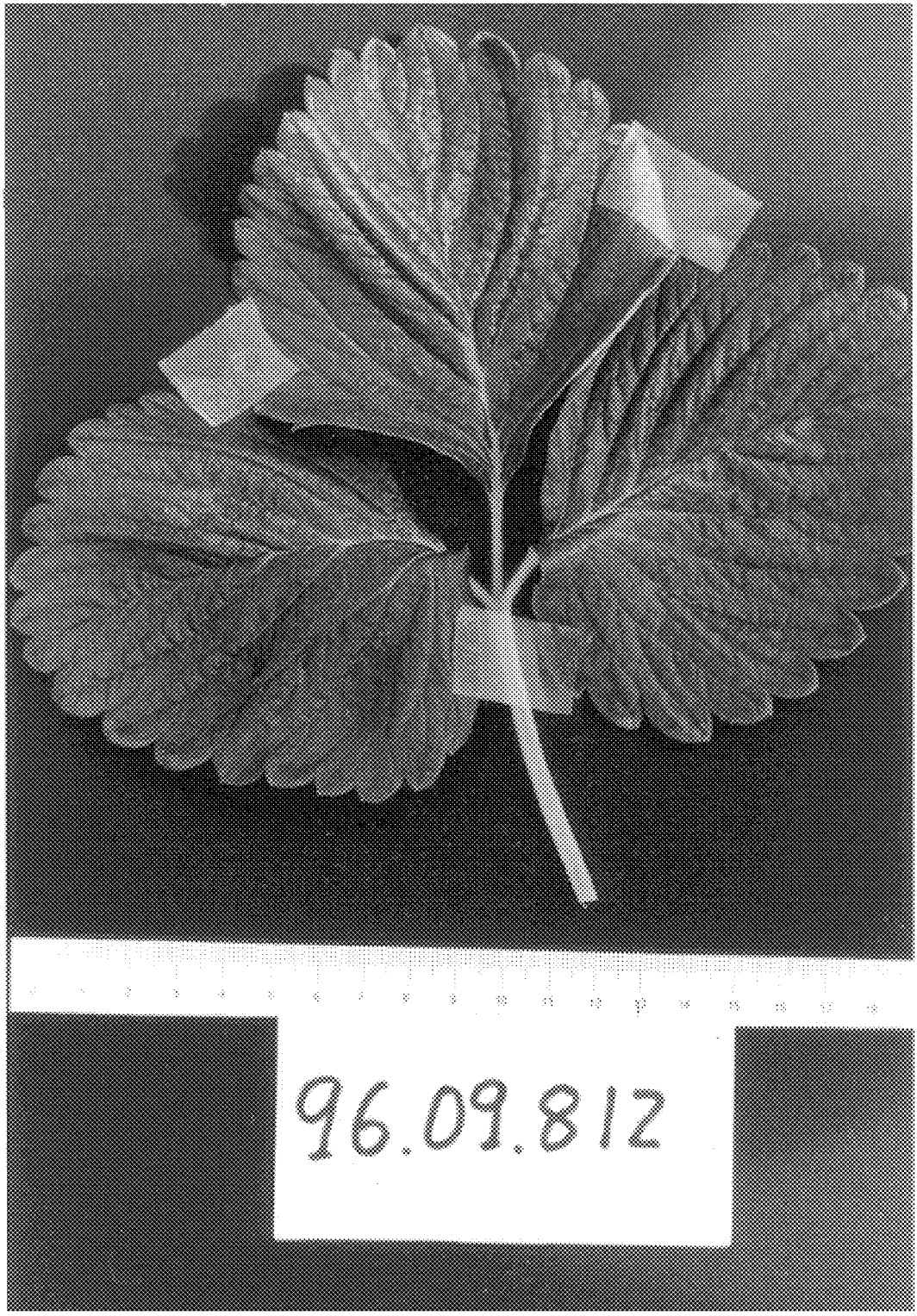
FIG. 3 shows a typical leaf of the new variety (designated 96.09.812) with more weak surface undulation of upperside and less dark green color of upperside than 'Camarosa'.
Figure 4:
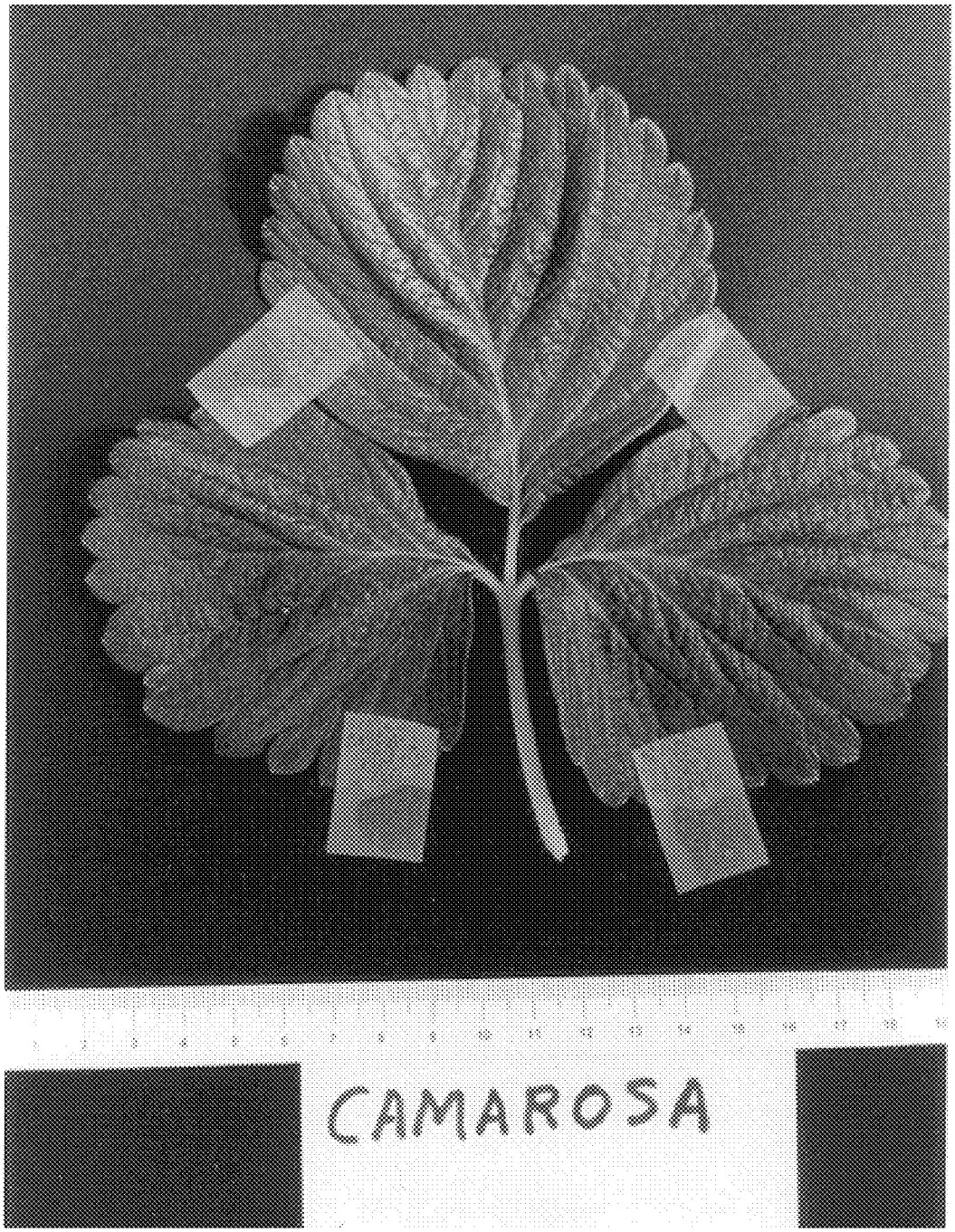
FIG. 4 shows a typical leaf of the 'Camarosa'.
Figure 5:
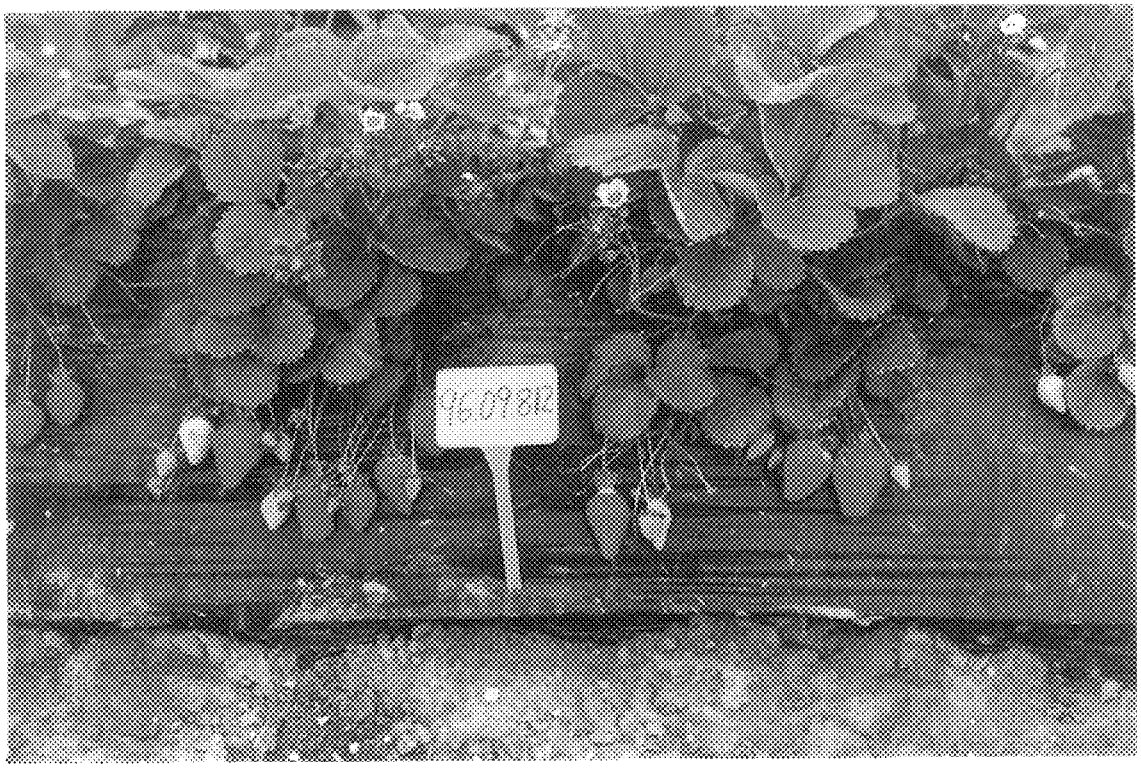
FIGS. 5 and 6 show the fruit against a background of the top surface of the foliage of the new variety (designated 96.09.812).
Figure 6:
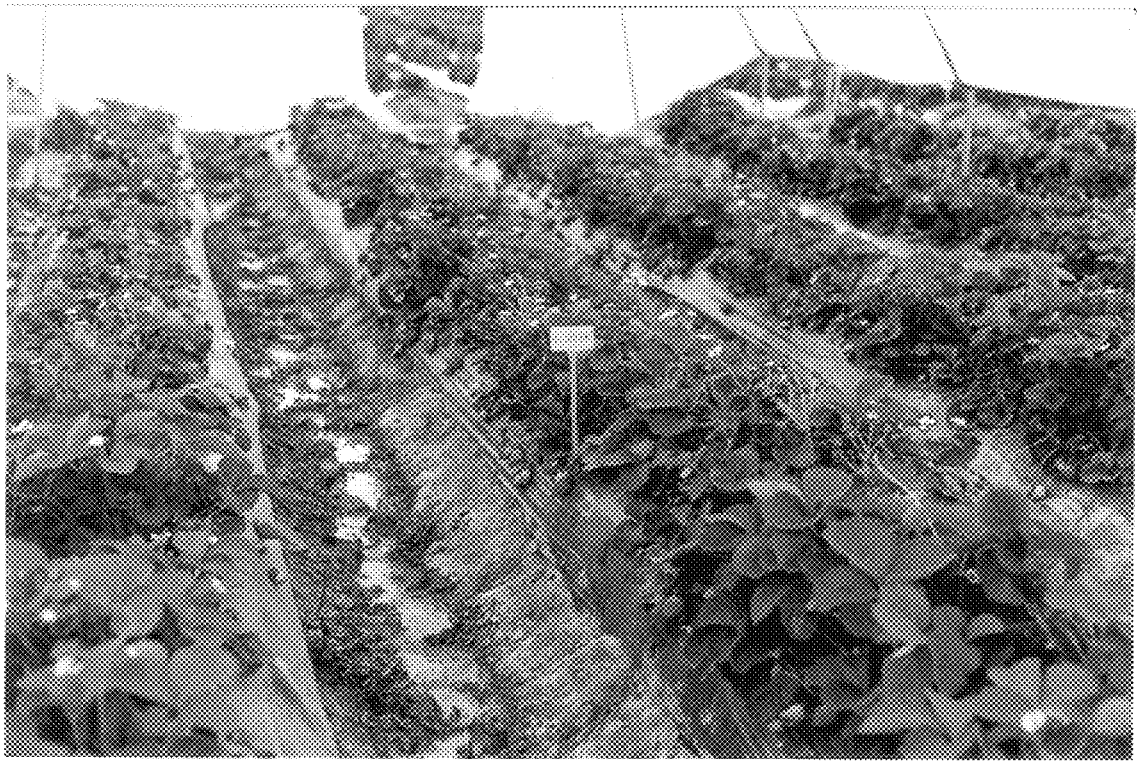
Figure 7:
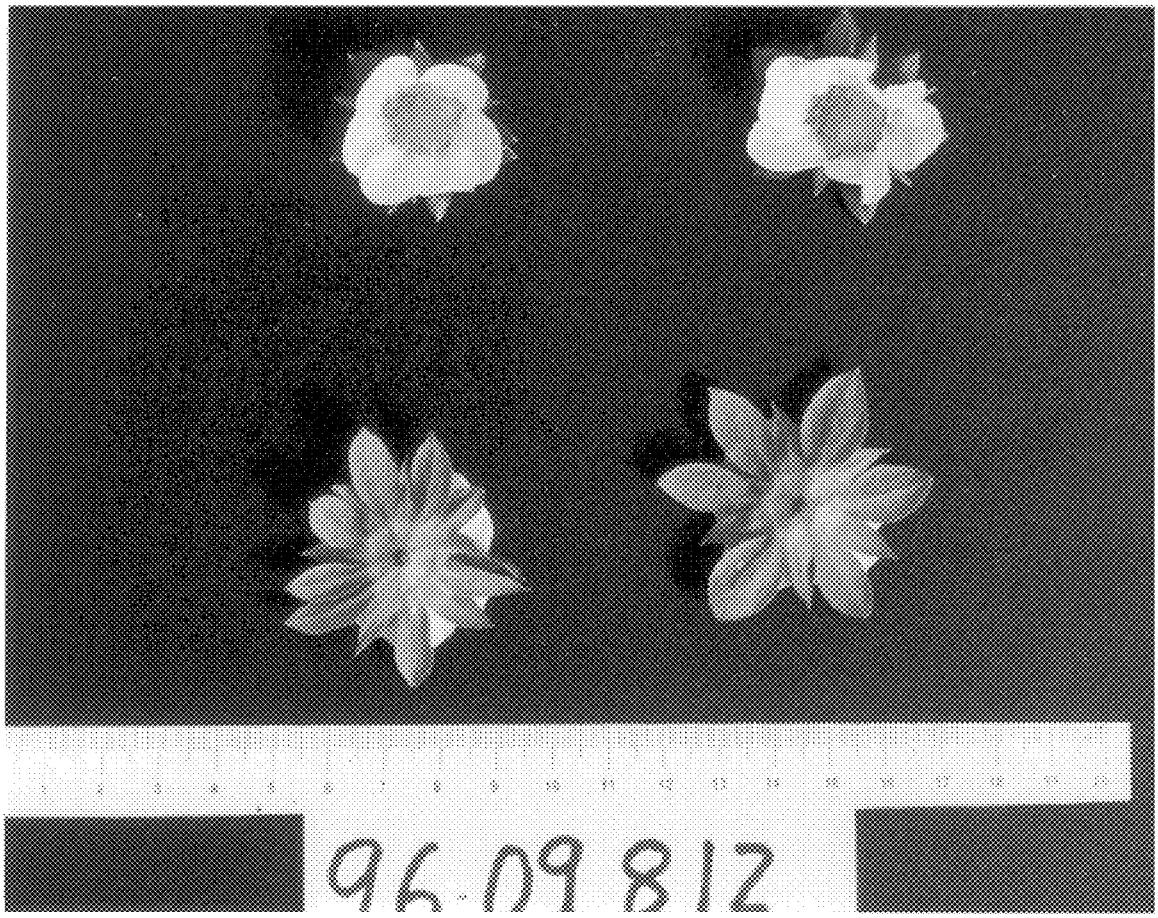
FIG. 7 shows the flower and reproductive organs of the new variety (designated 96.09.812).
Figure 8:
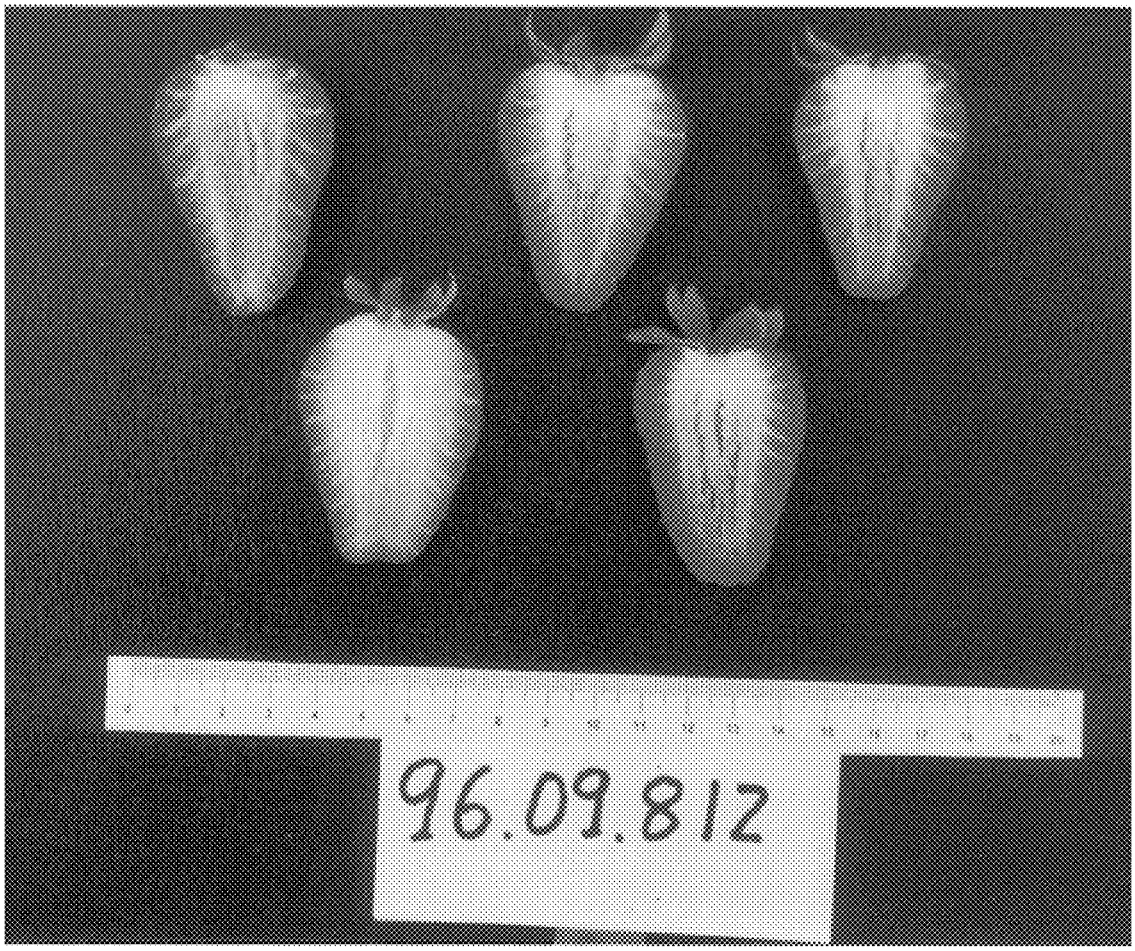
FIG. 8 shows typical fruit of the new variety (designated 96.09.812) in cross section illustrating the typical flesh and flesh coloration, conspicuous core and core cavity and conical shape.
Figure 9:
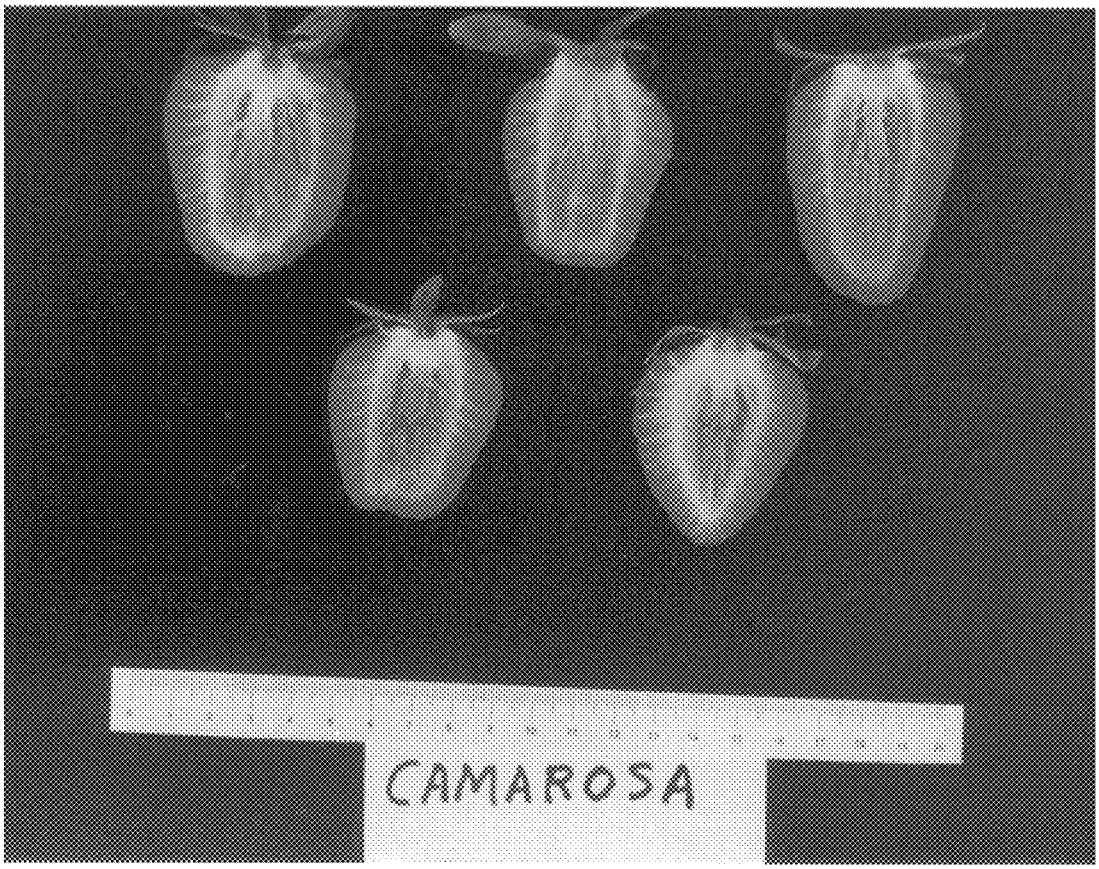
FIG. 9 shows typical fruit of the 'Camarosa' in cross-section illustrating the typical flesh and flesh coloration, conspicuous core and core cavity and almost cylindrical shape.
Figure 10:
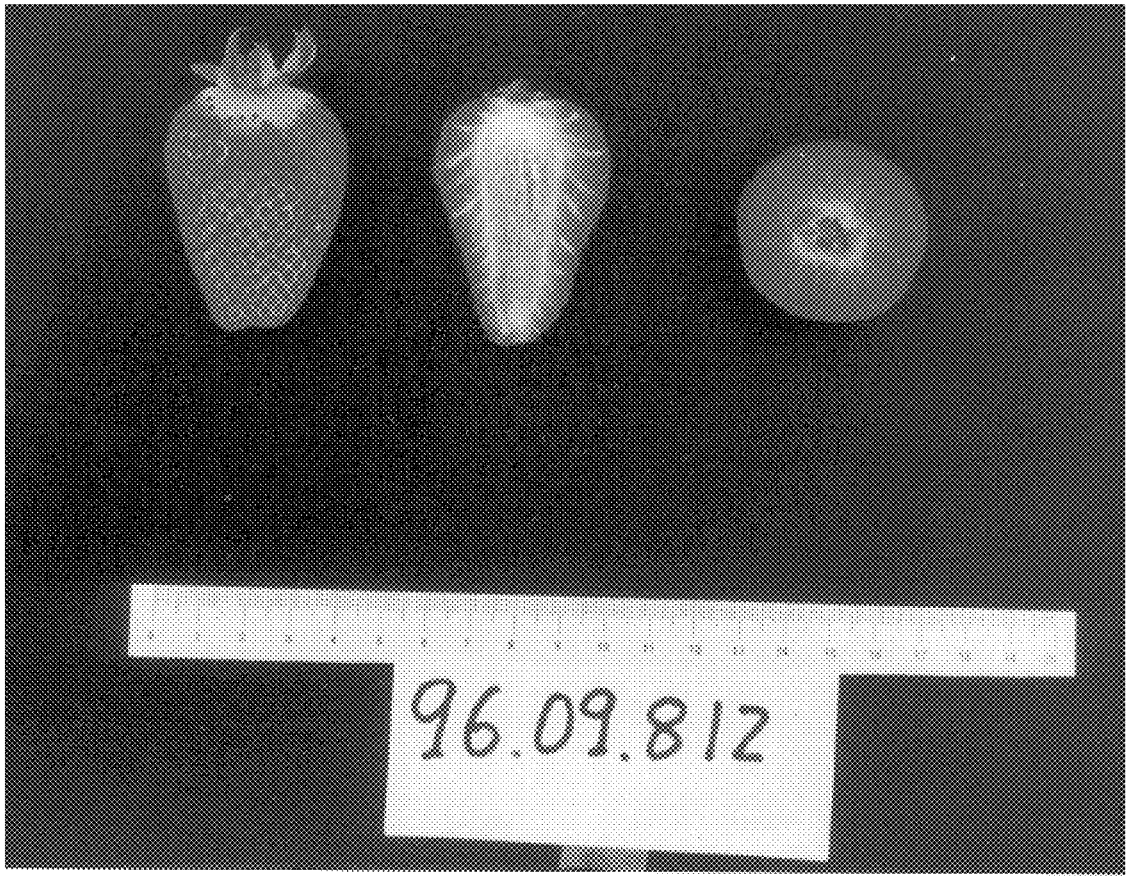
FIG. 10 shows whole and sliced, detached fruit of the new variety (designated 96.09.812) with the typical red color.
Figure 11:
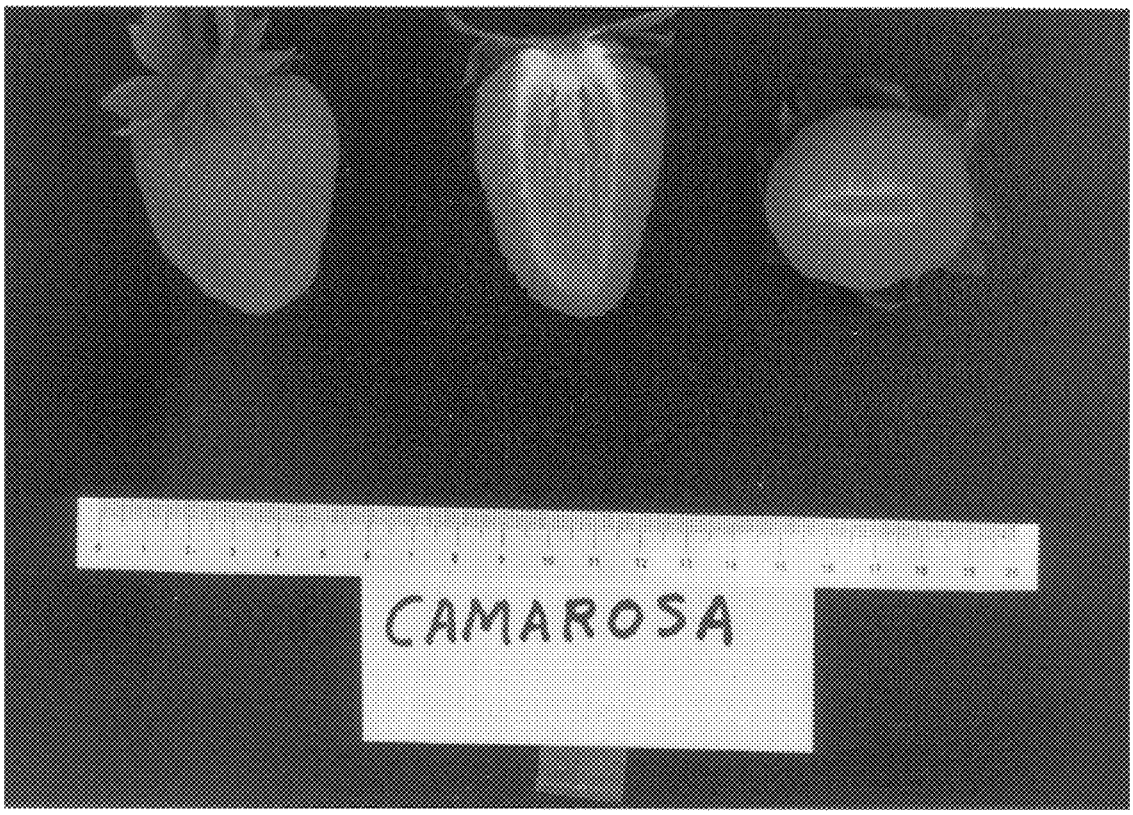
FIG. 11 shows whole and sliced, detached fruit of the 'Camarosa' with the typical red dark color.

Comparison with 'Camarosa': the new variety may be compared with 'Camarosa' by reference to the Figures, e.g., FIG. 1 with FIG. 2; FIG. 3 with FIG. 4; FIG. 8 with FIG. 9; and FIG. 10 with FIG. 11.

| Variety | February 25th | March 28th | April 24th | May 25th |
|---|---|---|---|---|
| 'CAMAROSA' | 49 | 266 | 521 | 706 |
| 'MILSEI' | 52 | 269 | 446 | 558 |
| 'TUDNEW' | 62 | 300 | 503 | 667 |
| 'PLARIONFRE' | 130 | 399 | 583 | 729 |

| Variety | 1ST + 2ND Quality Fruit | Total | Weight (g/fruit) |
|---|---|---|---|
| 'CAMAROSA' | 706 + 163 | 869 | 24 – 23 |
| 'MILSEI' | 558 + 163 | 721 | 23 – 22 |
| 'TUDNEW' | 667 + 131 | 798 | 24 – 23 |
| 'PLARIONFRE' | 729 + 136 | 865 | 22 |

Production totals of 1st Quality Fruit (to May 25th) and 2nd Quality Fruit in g/plant

| Variety | 1st quality | 2nd quality | TOTALS (1st + 2nd) | % 2nd quality |
|---|---|---|---|---|
| 'CAMAROSA' | 706 | 163 | 869 | 19% |
| 'MILSEI' | 558 | 163 | 721 | 23% |
| 'TUDNEW' | 667 | 131 | 798 | 16% |
| 'PLARIONFRE' | 729 | 136 | 865 | 16% |

$$\% \ 2^{nd} \text{ quality} = \frac{2^{nd} \text{ quality}}{\text{TOTAL}} \times 100$$

Weight (g/Fruit) at two dates March 28th and May 25th

| Weight (g/fruit) | March 28th | May 25th |
|---|---|---|
| 'CAMAROSA' | 24 | 23 |
| 'MILSEI' | 23 | 22 |
| 'TUDNEW' | 24 | 23 |
| 'PLARIONFRE' | 22 | 22 |

Weight is shown as the average weight per fruit of First Quality Fruit.

FRUIT ANALYSIS

| | 'CAMAROSA' | 'PLARIONFRE' (96.09.812) | 'CARTUNO' | 'TUDNEW' |
|---|---|---|---|---|
| Firmness (KG) | 0.46 | 0.19 | 0.36 | 0.28 |
| Humidity & Volatile Matter (%) | 92.41 | 90.62 | 92.35 | 92.24 |
| Dry Matter (%) | 7.59 | 9.38 | 7.65 | 7.76 |
| PH (to 20°) | 3.24 | 3.25 | 3.41 | 3.42 |
| Acidity as Anhydride | 0.76 | 0.69 | 0.70 | 0.61 |

-continued

| FRUIT ANALYSIS | | | | |
|---|---|---|---|---|
| | 'CAMAROSA' | 'PLARIONFRE' (96.09.812) | 'CARTUNO' | 'TUDNEW' |
| Citric (%) | | | | |
| Soluble Solids (°Brix) | 7.20 | 8.70 | 8.30 | 7.50 |
| Maturity Index | 9.47 | 12.61 | 11.86 | 12.29 |
| Content in Ascorbic Acid (ppm) | 610 | 770 | 570 | 610 |
| Dominant Tonality (nm) | 495 | 500 | 480 | 495 |
| Luminosity: Transmitance to 460 nm | 15.30 | 17.20 | 26.00 | 31.80 |

The following definitions apply:

Firmness: It is the fruit's resistance to penetration measured in Kilograms (Kg). The measure given has been obtained by the penetrometer ROZE Mod. Arbelette, with a 50 mm2 section head.

Dry matter: It is the weight of the residual left from the trituration of the fruit after the drying process at a temperature of 102° C.+2° C. until reaching constant weight.

$$(\%)\ \text{Dry Matter:}\ \frac{\text{Weight Dry Matter}}{\text{Weight Fresh Matter}} \times 100$$

Humidity & volatile matter: Represents the content in volatile matters and water of the fruits.

(%) Humidity & volatile matter: 100 — % Dry Matter.

Maturity index: Relation between Soluble solids and Acidity as Anhydride Citric.

Maturity index:

$$\frac{\text{Soluble solids}}{\text{Acidity as Anhydride Citric}}$$

TIME OF RIPENING

After planting as aforesaid, plants are grown in raised beds under-tunnel (small tunnel with small holes in plastic walls). Water and fertilizer were applied through drip irrigation. Time of ripening (50% of plants with ripe fruit) occurred about Jan. 12, 2000. First mature fruit was observed about Jan. 9, 2000, and maturity (15–20 gms/plant) is about January, 20.

GENERAL

The growing period in Huelva, Spain, where the observations were made, is between about January 25$^{th}$ and May 31$^{st}$ of each year, with a maximum production at about mid-April. 'PLARIONFRE' is a variety that benefits from induction to flowering by chilling, usually a few hours are sufficient, preferably at temperatures of 7° C. or less. Normally, the minimum number of hours is accumulated in the field during several days.

DISEASE RESISTANCE

No particular sensitivity to any disease or parasite has been observed for 'PLARIONFRE'.

The following additional information is provided to further describe the new variety:

Variety: 'PLARIONFRE,' Breeder Ref. 96.09.812.
Classification: Fragaria, L.
Plant:
- *Habit.*—Flat globose.
- *Density.*—Open.
- *Vigor.*—Medium.
- *Height.*—About 17 cm.
- *Width.*—About 24 cm.

Leaf:
- *Upperside.*—Near 143B to 143A.
- *Underside.*—Near 145D.
- *Length.*—About 10 cm.
- *Width.*—About 11 cm.
- *Cross-section.*—Slightly concave.
- *Leaf surface undulation or blistering.*—Weak.
- *Number of leaflets.*—Three only.

Stem characteristics:
- *Color.*—Near 145C.
- *Position of hairs.*—Upwards.
- *Length.*—About 10 cm.

Terminal leaflet:
- *Length/width ratio.*—As long as broad.
- *Length.*—About 6.5 cm.
- *Width.*—About 6.5 cm.
- *Shape of base.*—Obtuse.
- *Shape of teeth.*—Obtuse.

Petiole:
- *Position of hairs.*—Upwards.
- *Length.*—About 10 cm.

Stipule:
- *Anthocyanin coloration.*—Strong; anthocyanin coloration near 178C to 179A.

Stolons: Average length of stolon about 19 cm.
- *Number.*—Medium — about 7.
- *Anthocyanin coloration.*—Medium.
- *Thickness.*—Medium, about 3 mm.
- *Pubescence.*—Medium.
- *Color.*—Between near 145C to 144D; sometimes some stolons present a weak anthocyanin coloration near 179C to 179B.

Inflorescence: Position relative to foliage — Above.
Flower:
- *Size.*—Medium, flower bud average size about 3.5 cm., color near 143C to 143A.
- *Size of calyx relative to corolla.*—Larger; diameter of calyx or primary flower is approximately 4.3 to 4.7 cm.; diameter of calyx of secondary flowers is approximately 3.4 to 3.8 cm.; the calyx presents 6 to 7 sepals with lanceolate shape and 5 to 6 smaller sepals with pointed shape; color of the upper side of sepals is near 143B to 143A; color of underside of sepals is near 143D to 143C.

*Size of inner calyx relative to outer.*—Larger.

*Spacing of petals.*—Overlapping.

Flower characteristics:

*Diameter primary flowers.*—About 3.5 cm.

*Diameter secondary flowers.*—About 2.5 cm.

*Number of petals.*—Normally about 6 — No significant fragrance.

*Time from bloom to mature fruit* (*Huelva, Spain*).—Between about 35 to 40 days.

Stamens: Numerous stamens with pollen present, fertile and abundant, length about 4 to 5 mm., color near 155D.

Anthers: Usually similar in size, color near 12A to 13A.

Pollen: Abundant, color near 14B to 15B.

Pistils: Numerous, color near 12B to 13C.

Petal:

*Length and width.*—Length approximately 7 to 8 mm.; width approximately 8 to 9 mm.; shape slightly ovate; color white.

Pedicel: Length approximately 14 to 16 cm.; diameter approximately 2 to 3 mm.; color near 145C to 144D.

Peduncle: Diameter about 1.5 to 2 mm.; color near 145D to 145C.

Fruiting truss:

*Attitude.*—Semi-erect.

Fruit:

*Ratio of length/maximum width.*—Longer than broad.

*Color.*—Between near 43A to 42A.

*Peduncle length of inflorescence stem.*—Primary fruit between about 9 to 11 cm., secondary fruit between about 6 to 7 cm., color near 145C.

Primary fruit:

*Length.*—About 5.5 cm.

*Width.*—About 4 cm.

Secondary fruit:

*Length.*—About 4.5 cm.

*Width.*—About 3 cm.

*Size.*—Large.

*Predominant shape.*—Conical.

*Difference in shapes between primary and secondary fruits.*—Moderate.

*Band without achenes.*—Narrow.

*Unevenness of surface.*—Weak.

*Color.*—Between near 43A to 42A.

*Evenness of color.*—Slightly uneven.

*Glossiness.*—Strong.

*Insertion of achenes.*—Level with surface.

*Insertion of calyx.*—Level.

*Pose of the calyx segments.*—Reflexed.

*Size of the calyx in relation to fruit diameter.*—Same size.

*Adherence of calyx.*—Strong.

*Firmness.*—Firm.

*Color of flesh.*—Medium red — near 43A; lightening toward center near 43C to 41C.

Achenes: Color varies from near 35B to near 42D.

*Evenness of color of flesh.*—Even.

*Sweetness.*—Medium.

*Acidity.*—Medium.

*Time of flowering.*—Early.

*Time of ripening.*—Very early.

*Time of bearing.*—Not remontant.

*Chilling.*—Weak.

*Planting date.*—Oct. 22, 1999.

*10% flowering.*—Nov. 29, 1999.

*First mature fruits.*—Jan. 9, 2000.

*Maturity* (*15–20 gms/plant*).—Jan. 20, 2000.

TIME OF FLOWERING DATA

Date of planting Oct. 22, 1999, in Cartaya (Huelva), Spain, about 7° W, 37° N, 45 feet elevation. 10% flowering occurred about Nov. 29, 1999, with first mature fruits about Jan. 9, 2000, and maturity (15–20 g/plant) about Jan. 20, 2000.

Time of flowers (50% of plants at first flower): observed about Dec. 3, 1999.

STORAGE QUALITIES

'PLARIONFRE' fruit maintain their quality characteristics when keeping them in a frigo chamber at temperatures of about 2° C. during 48 hours. The fruit's color remains substantially the same.

I claim:

1. A new and distinct strawberry plant of the variety substantially as shown and described.

* * * * *